US00PP07870P

United States Patent [19]

Izsak et al.

[11] Patent Number: Plant 7,870

[45] Date of Patent: May 19, 1992

[54] STRAWBERRY PLANT SAAID

[75] Inventors: Eva Izsak; Shamai Izhar, both of Rehovot, Israel

[73] Assignee: State of Israel, Ministry of Agriculture, The Volcani Center, Bet Dagan, Israel

[21] Appl. No.: 735,970

[22] Filed: Jul. 25, 1991

Related U.S. Application Data

[63] Continuation of Ser. No. 491,758, Mar. 6, 1990, abandoned.

[30] Foreign Application Priority Data

Mar. 17, 1989 [IL] Israel ..... 1432/89

[51] Int. Cl.[5] ..... A01H 5/00

[52] U.S. Cl. ..... Plt./48

[58] Field of Search ..... Plt./48, 49

[56] References Cited

U.S. PATENT DOCUMENTS

P.P. 4,487 11/1979 Bringhurst et al. ..... Plt. 49
P.P. 5,262 7/1984 Voth et al. ..... Plt. 48
P.P. 5,263 7/1984 Voth et al. ..... Plt. 48
P.P. 5,264 7/1984 Bringhurst et al. ..... Plt. 48
P.P. 5,268 8/1984 Voth et al. ..... Plt. 48
P.P. 6,578 1/1989 Voth et al. ..... Plt. 48

FOREIGN PATENT DOCUMENTS

370/82 11/1984 Israel .

OTHER PUBLICATIONS

Izsak, E. (1978) Hassadeh 59:443–446.
Izsak, E. and Izhar, S. (1983) Hassadeh 63:2100–2103.
Izsak, E. and Izhar, S. (1984) Hassadeh 64:1774–1777.
Izsak, E. and Izhar, S. (1984) Hassadeh, 64:1778–1781.
Howard, C. M. and Albregts, E. E., 1980; HortScience 15(4):540.
Dubinsky, V., 1985; McSc. Thesis, The Hebrew University of Jerusalem; Rehovot, Israel (Hebrew and English translation).
Bringhurst, R. S. and Voth, V., 1989; Fruit Var. J. 43(1):12–19.

*Primary Examiner*—James R. Feyrer
*Attorney, Agent, or Firm*—Pennie & Edmonds

[57] ABSTRACT

A new and distinct variety of strawberry (Fragaria L.) called "Saaid" is disclosed. The variety is a cross between "Rachel" and "Douglas", which results in a variety that flowers several months earlier than other known strawberry varieties.

2 Drawing Sheets

This is a continuation of application Ser. No. 07/491,758 filed Mar. 6, 1990, now abandoned.

BACKGROUND OF THE INVENTION

The present invention relates to a new and distinct variety of strawberry (Fragaria L.) called "Saaid". The variety was developed from an organized scientifically designated breeding program carried out at the Agricultural Research Organization, the Volcani Center, Bet Dagan, Israel. The variety is the product of selection of seedlings resulting from crosses between the strawberry varieties "Rachel" and "Douglas". The variety was asexually vegetatively propagated through runners and the reproduction ran true.

SUMMARY OF THE INVENTION

The new variety "Saaid" resembles the variety "Douglas" and is able to grow in September and produce fruit starting in early December and lasting until summer. The production of fruit beginning in early December is two months earlier than any known variety of Fragaria L. The fruit of the "Saaid" variety is characterized by good taste, good shape and size as well as a long shelf life.

DETAILED BOTANICAL DESCRIPTION OF THE INVENTION

Figure 1:
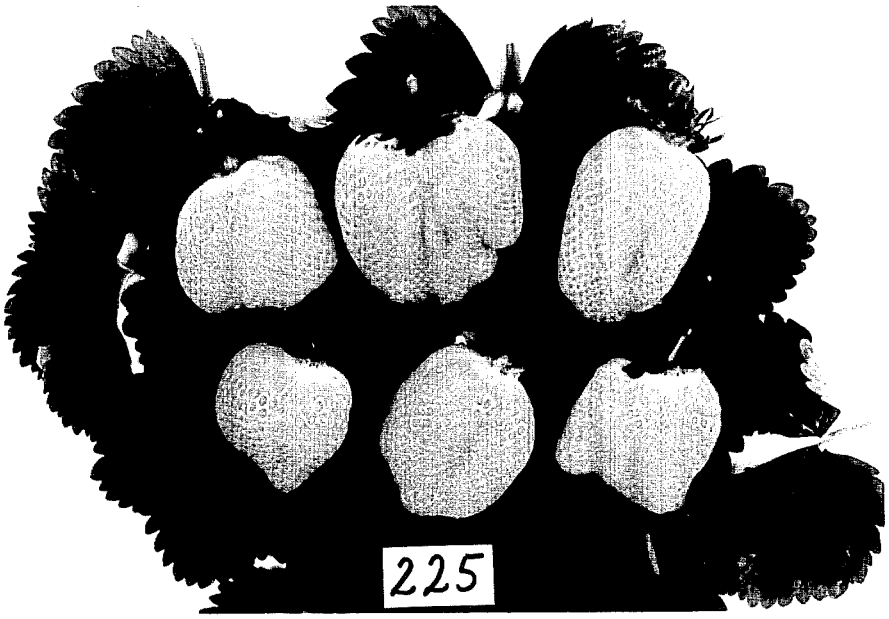
FIG. 1. Photograph of the "Saaid" variety illustrating the foliage and fruit.
Figure 2:
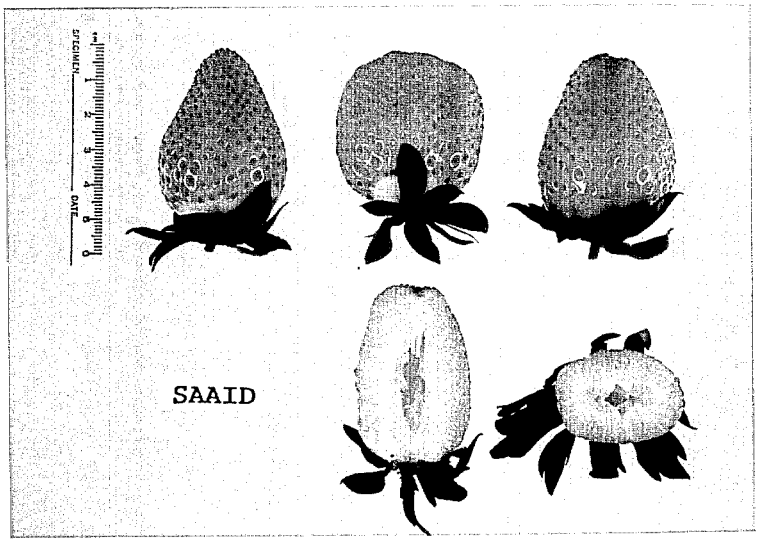
FIG. 2. Photograph of the "Saaid" variety illustrating the fruit.
Figure 3:
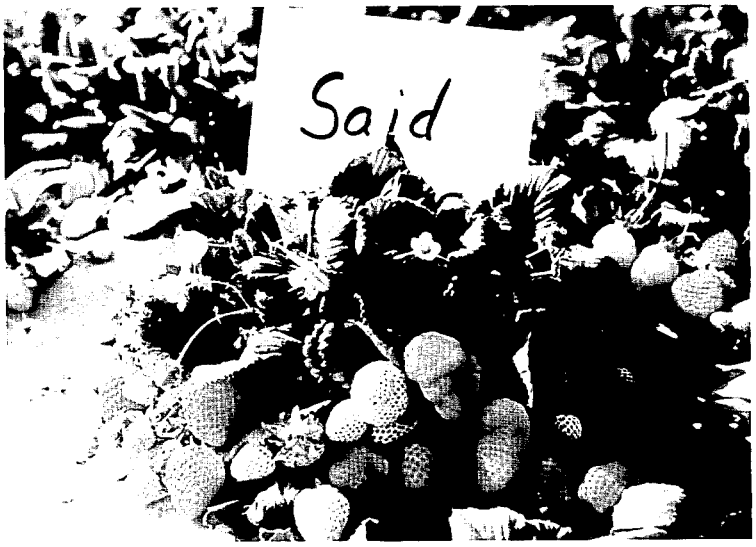
FIG. 3. Photograph of the "Saaid" variety illustrating the entire plant with both flowers and fruit.

The "Saaid" variety was grown in winter under polyethylene tunnels in Isreal. "Saaid" is a short day variety that flowers earlier than other known and available short day length strawberry varieties. Flowering and fruit production is not affected by the use of polyethylene wind tunnels. This production procedure is utilized in normal agricultural practices by the skilled artisan and does not involve temperature or light control. Mother plants were stored at 0° C. from January through April. They were then planted in the nursery without further treatment. Runners with plantlets were produced during summer. These young plantlets were collected from the nursery in September and transferred to raised beds. Average temperatures at that time of the year are 30° C. during the day and 22° C. at night. Water and fertilizers were applied through drip irrigation. An exaple of an optimum planting date is between September 20th to the 25th with the approximate date of flowering on November 4, and the approximate date of first fruiting on December 4. "Saaid" flowering is not induced by chilling, but by natural exposure to short day length (long nights) characteristic of late fall and early winter. Color readings described herein were taken under natural light conditions and color identifications were made by reference to The Royal Horticultural Society Colour Chart (R.H.S.C.C.) except where common terms of color definition are employed.

The pertinent characteristics of the present invention are presented in Table 1 and Table 2. Additionally, the variety "Saaid" (1) has no tendency toward fruit malformation; (2) disease resistance appears normal in that no particular problematic conditions arose during trials; and (3) the type of bearing is not remontant (e.g., "Saaid" blooms perpetuously, during late fall and winter).

The fruit is longer than broad, with primary, secondary and tertiary fruit of moderately distinct shape (Table 2). The fruit is firm with a red color (Table 2).

The variety "Saaid" flowers several months earlier than known strawberry varieties. One of the closest known varieties would be "Karina" (Table 1) as well as the new varieties under co-pending U.S. patent application Ser. Nos. 07/735,969 ("Sharon"), 07/735,695 ("Shalom"), 07/735,967 ("Smadar"), and 07/735,968 ("Dorit"). Additionally, early flowering results in early fruit production for "Saaid" and the four co-pending varieties (Table 3). Total Soluble Solids (TSS), percent acidity and aroma are presented in Table 4 by comparison to the varieties listed in Table 3.

TABLE 1

PLANT CHARACTERISTICS OF "SAAID"

| MORPHOLOGICAL TRAIT | DESCRIPTION[a] | COMPARABLE VARIETY[b] |
|---|---|---|
| Classification | Botanical-Fragaria L. | |
| Plant habit | Globose | "Gorella" |
| Plant density | Dense | "Talisman" |
| Plant vigor | Strong | "Grande" |
| Leaf: | | |
| a) Length | 17-18 cm | |
| b) Width | 11-14 cm | |
| c) Color | Green Group 146 A (RHSCC) | |
| 1) Upper Side: | Dark Green | |
| d) Blistering | Weak | |
| e) Cross-section | Concave | |
| f) # of leaflets | Three only | |
| Terminal leaflet | | |
| a) Length/Width ratio | Longer than broad | |
| b) Shape of base | Acute | |
| c) Shape of teeth | Rounded | |
| d) Length | 7-8 cm | |
| e) Width | 5-6 cm | |
| Flower | | |
| a) Size | Medium | "Gorella" |
| b) Size of calyx to corolla | Same Size | |
| c) Size of inner calyx versus outer calyx | Same Size | |
| d) Spacing of petals | Overlapping | |
| e) Petal length/width | As load as broad | |
| f) Time of flowering | Early to Medium | "Karina"[c] |
| Stolon | | |
| a) Number | Medium | "Gorella" |
| b) Thickness | Medium | |
| c) Pubescence | Weak | |
| d) Anthocyanin coloration | Strong | |
| Petiole | | |
| a) Pose of hairs | Outwards | |
| b) Length | 10-12 cm | |
| Inflorescence | | |
| a) Position relative to foliage | Level | |

[a]The description of "Saaid" is based on the test guidelines for Fragaria L. of the International Union for the Protection of New Plant Varieties, (UPOV).
[b]Only characteristics which are relevant for comparing varieties are listed.
[c]"Saaid" flowers at the beginning of November. One of the earliest known varieties for comparison is "Karina", which flowers in January.

TABLE 2

FRUIT CHARACTERISTICS OF "SAAID"

| CHARACTERISTIC | DESCRIPTION |
|---|---|
| Time of ripening | early |
| Ratio of length/maximum width | longer than broad |
| Primary Fruit[a] | Bi-conical |
| Length | 43-50 mm |
| Width | 30-36 mm |
| Secondary Fruit | Bi-conical |
| Length | 33-37 mm |
| Width | 27-32 mm |
| Tertiary Fruit | Conical |
| length | 28-30 mm |
| width | 25-26 mm |
| Size | Large |
| Brand without achenes | Narrow |
| Unevenness of surface | Weak |
| Color | Red |
| Evenness of color | Even |
| Glossiness | Strong |
| Insertion of achenes | Level with surface |
| Insertion of calyx | Level with surface |
| Pose of calyx segments | Reflexed |
| Size of calyx in relation to fruit diameter | Larger |
| Adherance of calyx | Strong |
| Firmness | Firm |
| Color of Flesh | Medium Red |
| Evenness of flesh color | Uneven |
| Sweetness[b] | Strong |
| Color | 42BC circa (RHSCC) |
| Taste[b] | Good |

[a]There is a marked difference between the shape of the primary, secondary and tertiary fruit.
[b]See Table 4.

TABLE 3

COMPARATIVE YIELD OF "SAAID"[a]

| | Nov. | Dec. | Jan. | Feb. | Mar. | Apr. |
|---|---|---|---|---|---|---|
| Saaid | 0 | 70 | 100 | 100 | 100 | 100 |
| Sharon[b] | 40 | 60 | 80 | 80 | 80 | 80 |
| Shalom[c] | 50 | 70 | 80 | 100 | 100 | 70 |
| Smadar[d] | 50 | 70 | 100 | 100 | 100 | 50 |
| Dorit[e] | 30 | 70 | 100 | 100 | 100 | 100 |
| Douglas[f] | 0 | 0 | 40 | 150 | 150 | 150 |
| Chandler[g] | 0 | 0 | 30 | 150 | 150 | 120 |

[a]Average yield in g/m$^2$ in Ramat Hadar, Israel (1989-90). The time of ripening for "Saaid" fruit is early to medium.
[b]U.S. Application Ser. No. 07/735,969. The time of ripening for "Sharon" fruit is very early.
[c]U.S. Application Ser. No. 07/735,695. The time of ripening for "Shalom" fruit is early.
[d]U.S. Application Ser. No. 07/735,967. The time of ripening for "Smadar" fruit is very early to early.
[e]U.S. Application Ser. No. 07/735,968. The time of ripening for "Dorit" fruit is early.
[f]U.S. Plant Pat. No. 4,487. The time of ripening for "Douglas" fruit is late.
[g]U.S. Plant Pat. No. 5,262. The time of ripening for "Chandler" fruit is late.

TABLE 4

COMPARATIVE FRUIT CHARACTERISTICS OF "SAAID"

| | T.S.S.[a] in % | Acidity[b] in % | Aroma | Taste |
|---|---|---|---|---|
| Saaid | 8.0-9.0 | 1.0 | 3 | Normal |
| Sharon[c] | 6.5-7.0 | 1.0 | 3 | Slightly Acidic |
| Shalom[d] | 8.0-9.0 | 1.0 | 4 | Normal |
| Smadar[e] | 8.5-9.5 | 1.0 | 5 | Good |
| Dorit[f] | 8.5-9.5 | 1.0 | 5 | Good |
| Douglas[g] | 6.5-7.0 | 0.8 | 3 | Slightly Acidic |
| Chandler[h] | 6.5-7.0 | 0.8 | 3 | Slightly |

TABLE 4-continued

| COMPARATIVE FRUIT CHARACTERISTICS OF "SAAID" | | | | |
|---|---|---|---|---|
| | T.S.S.[a] in % | Acidity[b] in % | Aroma | Taste |
| | | | | Acidic |

[a]Total Soluble Solids expresses fruit sweetness and was determined with a refractometer.
[b]Percent of acidity was determined as follows: 2 cc of juice extract was mixed with 20 cc of water. Five drops of fenolfthaleinen was added and the mixture was titrated with NaOH. The percent acidity is calculated as the quantity of NaOH (cc) × 0.32.
[c]U.S. Application Ser. No. 07/735,969.
[d]U.S. Application Ser. No. 07/735,695.
[e]U.S. Application Ser. No. 07/735,967.
[f]U.S. Application Ser. No. 07/735,968.
[g]U.S. Plant Pat. No. 4,487.
[h]U.S. Plant Pat. No. 5,262.

What is claimed is:

1. A new distinct variety of strawberry substantially as illustrated and described and distinguished as being able to grow in September and produce fruit starting in early December and lasting until summer, with fruit having a good taste and shape and a long shelf life.

* * * * *